United States Patent [19]

Jurgens, Jr. et al.

[11] Patent Number: 4,718,463
[45] Date of Patent: Jan. 12, 1988

[54] METHOD OF PRODUCING PREFILLED STERILE PLASTIC SYRINGES

[75] Inventors: Raymond W. Jurgens, Jr., Manchester, Mo.; Richard G. Johnson, Raleigh, N.C.; Leroy R. Nadler, Maryland Heights, Mo.

[73] Assignee: Mallinckrodt, Inc., St. Louis, Mo.

[21] Appl. No.: 938,828

[22] Filed: Dec. 8, 1986

Related U.S. Application Data

[63] Continuation-in-part of Ser. No. 811,456, Dec. 20, 1985.

[51] Int. Cl.$^4$ ............................................. B65B 3/04
[52] U.S. Cl. ....................................... 141/11; 141/91; 141/326; 134/22.1; 134/169 R; 422/25
[58] Field of Search ..................... 141/1-12, 141/85-92, 325, 326, 327, 18-29; 134/22.1, 169 R; 422/25-28

[56] References Cited

U.S. PATENT DOCUMENTS

| | | | |
|---|---|---|---|
| 3,623,474 | 11/1971 | Hellman et al. | 128/2 R |
| 3,701,345 | 10/1972 | Hellman et al. | 128/2 R |
| 4,006,736 | 2/1977 | Kranys et al. | 128/2 A |
| 4,273,263 | 6/1981 | Voegele et al. | 141/91 |

OTHER PUBLICATIONS

Amsco Tech Data Sheet, Amsco—1980.

Primary Examiner—Houston S. Bell, Jr.
Attorney, Agent, or Firm—Bernard, Rothwell & Brown

[57] ABSTRACT

There is disclosed a process for producing sterilized prefilled plastic syringes avoiding plastic deformation and distortion. The plastic barrels are subjected to repeated water jet washing steps to remove contaminants and depyrogenate the barrels. Tip seals and pistons are subjected to removal of debris and pyrogens and destruction of microbial contaminants. After the tip is assembled on the nozzle of the barrel, the barrel is filled with contrast media through its open end, after which the piston is assembled in the open end to seal the syringe and its contents. The assembled and sealed syringe is then subjected to autoclaving to sterilize the syringe and its contents, without deformation of the plastic syringe or a loss of integrity to the closed media/syringe system.

3 Claims, 4 Drawing Figures

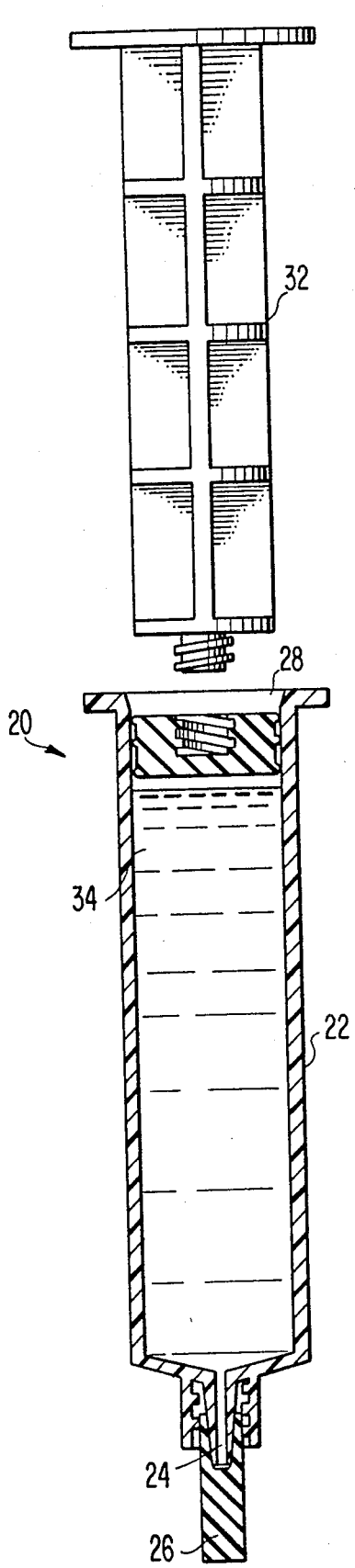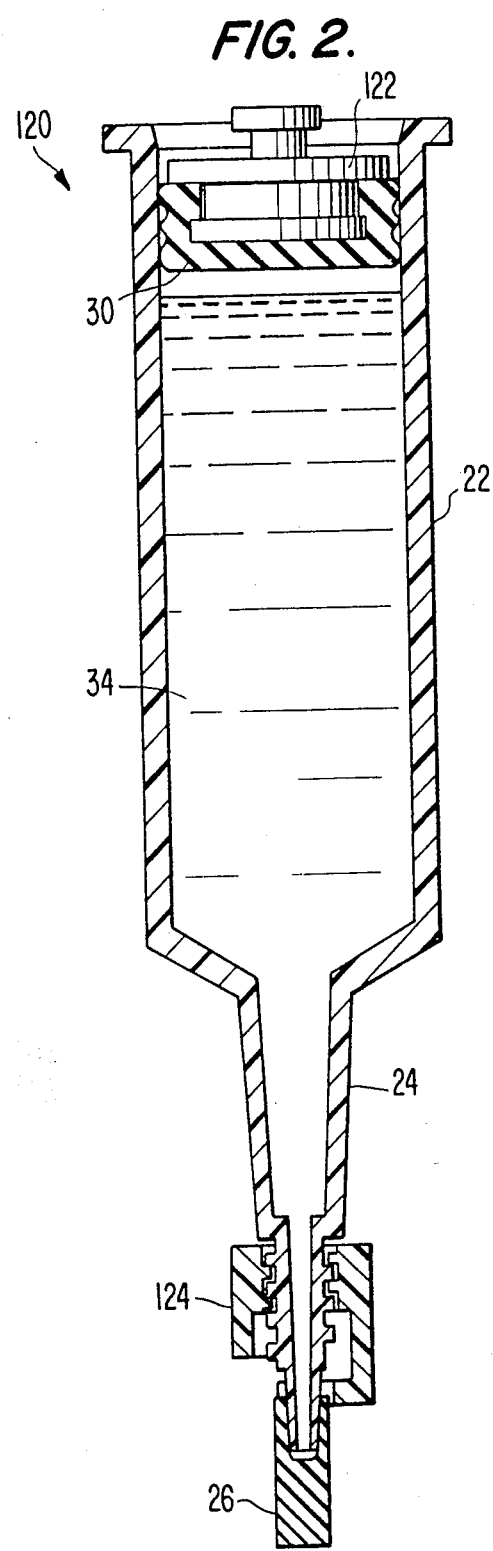

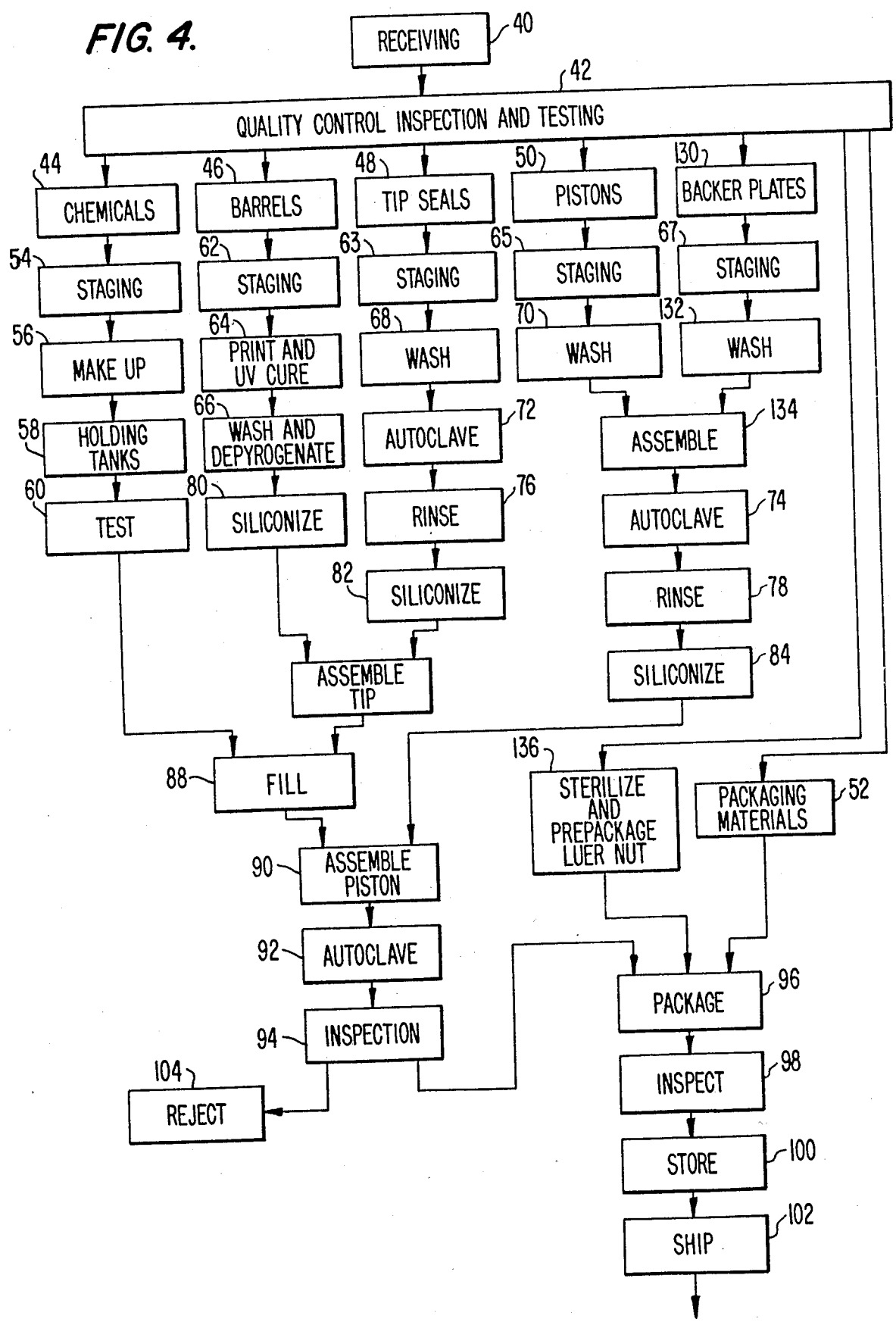

METHOD OF PRODUCING PREFILLED STERILE PLASTIC SYRINGES

CROSS REFERENCE

This application is a continuation-in-part of U.S. Ser. No. 811,456, filed Dec. 20, 1985.

TECHNICAL FIELD

The present invention relates to processes for producing prefilled sterile, plastic syringes containing liquid materials suitable for injection in the diagnosis and treatment of medical conditions, and particularly for producing prefilled syringes containing contrast media for injection into blood vessels during uroangiographic procedures.

DESCRIPTION OF THE PRIOR ART

The prior art contains processes for producing prefilled sterile glass syringes wherein the syringe parts are washed and sterilized prior to assembly, filling and sealing with a piston. Then the assembled and filled syringes are autoclaved to sterilize the syringe contents. Generally, the sterilizing of the syringe parts including glass barrels prior to assembly is performed by heating. Plastic syringes, or syringes with barrels made of synthetic resins, are softened and warped by heat, and thus prior art plastic syringes were sterilized by non-heating methods, such as gas sterilization techniques. Also, the plastic syringes were believed unable to withstand autoclaving in the sterilization of the contents of prefilled syringes. Where the size and relative cost of plastic and glass syringes made the employment of plastic syringes desirable, unfilled sterile plastic syringes were employed by filling with sterilized contrast media, or other diagnostic or treatment material, during the injection procedure thus increasing the time required for the procedure as well as increasing the risk of contamination and introduction of pyrogens.

SUMMARY OF THE INVENTION

The invention is summarized in a method of producing a prefilled, sterile plastic syringe having a molded plastic barrel with an open end and a nozzle at the opposite end, a tip seal closing the nozzle, and a piston slidable in the barrel and sealing the open end of the barrel to retain a liquid therein. The method includes the steps of removing debris and other contaminants from the tip seal and piston; destroying microbial contaminants on the tip seal and piston; washing the barrel with a multiplicity of jets of water to remove debris and pyrogens from the barrel; applying a layer of lubricant to the barrel, the tip seal and the piston; assembling the tip seal on the nozzle of the barrel; filling the barrel through its open end with a desired quantity of liquid material; assembling the piston in the open end of the barrel to complete the enclosure and to seal the open end of the syringe; and autoclaving the assembled and sealed syringe to sterilize the syringe and its contents, while maintaining a pressure on the outside surfaces of the syringe at least equal to the pressure of the syringe contents during autoclaving.

In a preferred embodiment of the invention, the method comprises washing the tip seal and piston to remove debris and other contaminants; autoclaving the washed tip seal and piston to destroy bacteria and other contaminants; rinsing the autoclaved tip seal and piston to remove loosened contaminants; washing the barrel with a multiplicity of jets of water to remove debris and pyrogens from the barrel; applying a fine mist of silicone lubricant to the barrel; assembling the tip seal on the nozzle of the barrel; filling the barrel through its open end with a desired quantity of liquid material; assembling the piston in the open end of the syringe; and autoclaving the assembled and sealed syringe to sterilize the syringe and its contents, while maintaining a pressure on the outside surfaces of the syringe at least equal to the pressure of the syringe contents during autoclaving.

An object of the invention is to provide a method of producing sterile, prefilled plastic syringes, and particularly plastic syringes containing sterilized contrast media.

An advantage of the invention is that the present process enables reducing the time spent in medical procedures such as angiographic procedures. Another advantage of the invention is that the risk of injecting pathogens or contaminants is reduced during injection procedures.

One feature of the invention is that the process provides a unique combination of steps which enable the production of sterile prefilled plastic syringes.

Other objects, advantages and features of the invention will be apparent from the following description of the preferred embodiments taken in conjunction with the accompanying drawings wherein:

BRIEF DESCRIPTION OF THE DRAWINGS

FIG. 1 is a sectional view of a prefilled sterile plastic syringe produced in accordance with the invention.

FIG. 2 is a sectional view of a variation of the prefilled sterile plastic syringe produced in accordance with the invention.

FIG. 4 is a process flow diagram of a preferred embodiment of a method for producing the prefilled sterile plastic syringe of FIG. 2.

DESCRIPTION OF THE PREFERRED EMBODIMENTS

Figure 3:
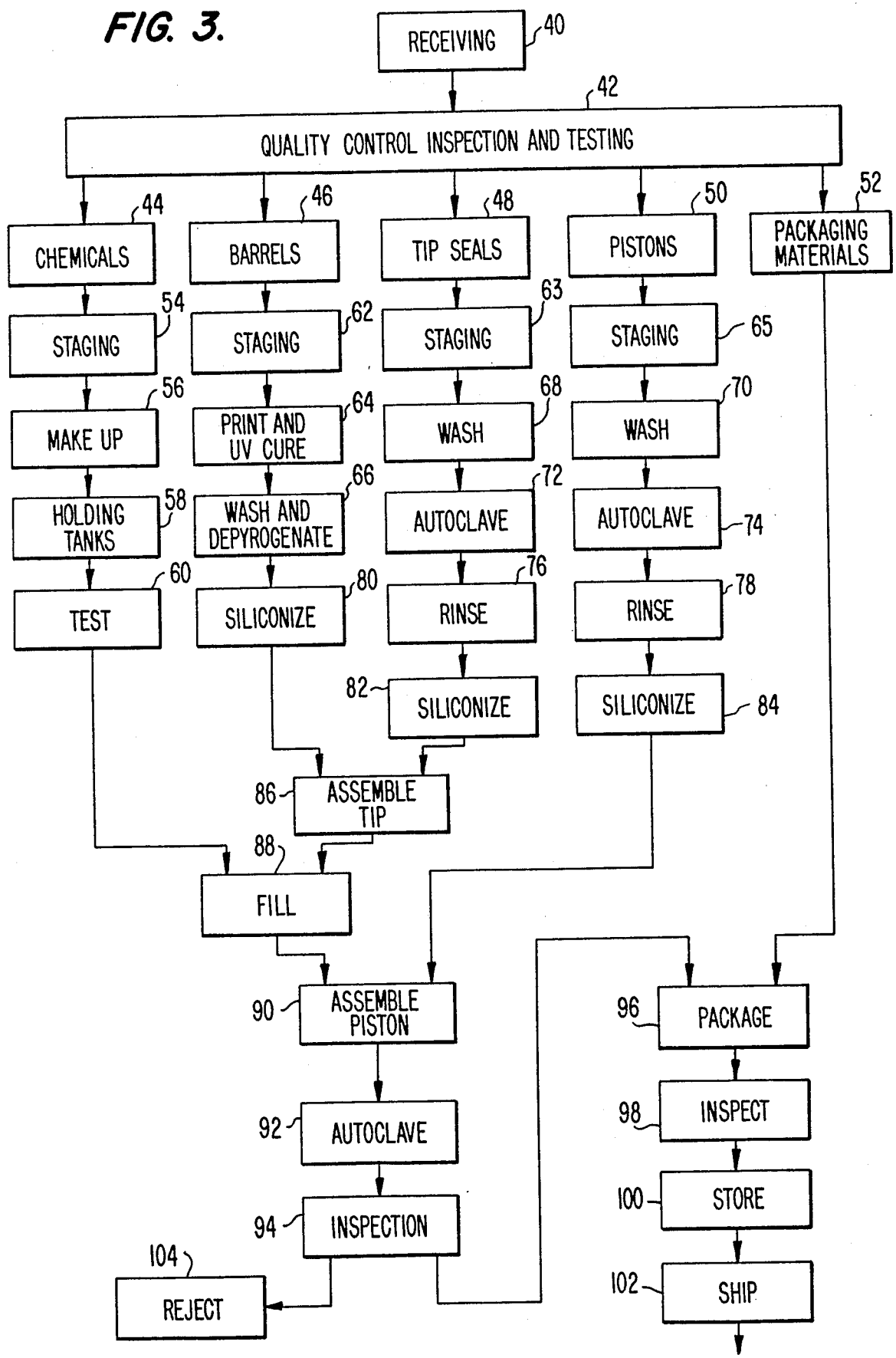
FIG. 3 is a process flow diagram of a preferred embodiment of a method for producing the prefilled sterile plastic syringe of FIG. 1.

As shown in FIG. 1, a prefilled sterile plastic syringe indicated generally at 20 produced in accordance with one embodiment of the invention includes a plastic barrel 22 having a nozzle 24 at one end which is closed by a tip seal 26. An open end 28 of the barrel 22 is closed and sealed by a rubber piston 30 which can be operated by a handle 32 for expressing the contents 34 through the nozzle 24. The parts of the syringe are individually manufactured. The syringe barrel 22 is produced by a suitable plastic-forming process such as injection molding of a suitable polymer such as polypropylene, or a co-polymer of polypropylene and polyethylene. The tip seal 26 and piston 30 are likewise produced by injection molding a suitable elastomeric plastic or rubber material to the desired shapes.

In a process for producing the prefilled sterile syringe 20 as illustrated in FIG. 3, quantities of the various parts of the syringe 20 are received at step 40 and passed to quality control inspection and testing procedure 42 where suitable inspection and testing of the chemicals utilized to make up the contrast medium, and inspection and testing of the barrels 22, the tip seals 26, the pistons 30, as well as the packaging materials are performed to insure that these chemicals and parts meet suitable standards for producing prefilled packaged and completed syringes. After passing through the inspection and testing procedure 42, the chemicals, barrels 22, tip seals 26, pistons 30 and packaging materials are suitably inventoried and stored in steps 44, 46, 48, 50 and 52. From the step 44, the chemicals pass through the staging step 54 to a make-up step 56 where the chemicals are made up into the liquid contrast media which is then passed to holding tanks 58 prior to being tested at 60. The barrels 22, after passing through a staging step 62 are printed on the outside with an ink which is cured with ultraviolet radiation in step 64. After printing and curing of the ink, the barrels are passed to a washing and depyrogenation step 66 wherein the barrels are inverted and subjected to a multiplicity, e.g., ten, successive high velocity water jet washings. By repeated washing of the barrels with relatively strong water jets, contaminants, including any pyrogens that are present in the barrels, are removed.

The tip seals 26 and the pistons 30 from their receiving storage steps 48 and 50 pass through the staging steps 63 and 65 prior to removing debris and other contaminants. In the preferred embodiment illustrated in FIG. 3, debris and contaminants are removed from the tip seals 26 and pistons 30 in washing steps 68 and 70 where they are subjected to washing to remove most contaminants.

Alternatively, debris and contaminants can be removed from the tip seals 26 and pistons 30 by other methods such as subjecting them to high frequency vibrations. This can be accomplished using known procedures such as, for example, by subjecting them to ultrasound vibrations or by causing high frequency pulses of air to impinge on the surfaces of the tip seals 26 and pistons 30 from pneumatic nozzles. Another method of removing debris and contaminants from the tip seals 26 and pistons 30 can be accomplished by washing them in liquid freon under pressure to dissolve and remove particles adhered to their surfaces.

After removal of debris and other contaminants, the tip seals 26 and pistons 30 pass to respective autoclave steps 72 and 74 where they are heated by steam under pressure to a temperature in the range from 120° to 125° C. to destroy viable microorganisms and remove contaminants on the tip seals 26 and pistons 30.

Alternatively, microorganisms can be destroyed on the tip seals 26 and pistons 30 by other known means, provided only that they do not adversely affect the materials of construction. For example, they can be sterilized by exposure to radiation, preferably from a radiation source such as cobalt-60. Another suitable method for destroying microbial contaminants is by treating the tip seals 26 and pistons 30 with an antimicrobial chemical agent. Ethylene oxide gas may be employed as the antimicrobial agent; however, care must be taken to remove all the ethylene oxide from the surfaces of the tip seals 26 and pistons 30 by aeration and/or the application of vacuum.

After autoclaving, the tip seals 26 and pistons 30 are rinsed in respective steps 76 and 78 to remove the loosened contaminants. From steps 66, 76 and 78, tip seals 26 and pistons 30 are passed in the preferred embodiment to respective siliconizing steps 82 and 84 where the parts are soaked in a fine water emulsion siliconization bath to enable their easy assembly. The barrels 22 are sprayed at siliconizing step 80 with a fine mist of a selected liquid silicone. While silicone is the preferred lubricant, other lubricants can be used, provided they are pharmaceutically acceptable and inert to the materials of construction. One can mention as suitable lubricants, paraffinic waxes such as refined beeswax and fixed oils such as cottonseed oil. These lubricants can be applied by spraying in a fine mist or by any other method of application which is capable of applying a thin layer of lubricant. The barrels 22 may then be treated to remove the adherence of excess lubricant to the barrels 22 by such processes as autoclaving or heating.

The tip seals are assembled onto the nozzles 24 of the barrels in step 86 after the siliconizing. The empty barrels with tip caps on are purged with nitrogen prior to filling with contrast media. The barrels are filled in step 88 with contrast media 34 held in step 58 after the contrast media has been sampled and tested in step 60. Following the filling of the barrels in step 88 to the desired volume, the pistons 30 are then assembled in the open upper ends 28 of the barrels in step 90 to seal the contrast media in the syringe. The assembly of the pistons includes the evacuation of air from the barrels via a vacuum system so that the pistons 30 can be inserted within the open upper ends 28 of the barrel with a selected amount of inert gas above the level of the liquid contents 34. At this stage, a reject mechanism discards those syringe barrels which were without a tip cap, or a piston, and/or otherwise improperly positioned or not ready for the next step. After the pistons have been assembled in step 90 the syringes are passed to an autoclave in step 92 where the syringes and their contents are heated under pressure in a steam/air mixture autoclave and sterilized to an $F_o$ value of 20 or more, dependent on the contents to be sterilized. After sterilization, the syringes are inspected in step 94 and the syringes are passed through packaging step 96, inspecting step 98 to storage in step 100 from which they are shipped in step 102. Syringes which do not pass the inspection 92 are rejected at 104 and discarded.

In a variation of the sterile prefilled syringe indicated generally at 120 in FIG. 2, the piston 30 has a backer plate 122 which is designed for being gripped and driven by a conventional power injecting machine (not shown). Additionally, the modified syringe 120 includes a nut 124 which is threaded onto the nozzle 24 and is configured for securing a luer of a catheter (not shown) to the nozzle 24 in a conventional manner.

As shown in FIG. 4, the process for producing the syringe 120 differs from the process of FIG. 3 by including a storage step 130 and washing step 132 for the backer plates 122, as well as an assembly step 134 wherein the backer plate 122 is assembled in the piston 130 prior to the autoclaving step 74. The luer nut 124 is sterilized and prepackaged at step 136. At step 96, the sterilized prepackaged luer nut 124 is placed into a form-filled seal tray together with the assembled prefilled syringe. Alternatively, the luer nut 124 may be assembled onto the syringe prior to packaging.

The combination of steps forming the process of FIGS. 3 and 4 is able to produce sterile prefilled plastic syringes which have heretofore been impossible to produce utilizing standard production procedures. Plastic syringes, and particularly the plastic barrels 22, have been subject to deformation when heat-sterilizing the syringes. The present process substitutes a multiple washing and depyrogenation step 66 which is accomplished by repeated water jet washings. Furthermore, it has been found that when the syringe is filled and sealed and then subjected to the autoclaving step 92 to sterilize the sealed contents of the syringe, the barrel 22 is not subject to distortion as indicated by the prior art. To avoid barrel distortion, the filled syringe is autoclaved by steam/air mixture autoclave which selectively adds compressed air during the autoclave cycle as necessary in order to maintain a pressure in the autoclave, i.e., a pressure on the outer surfaces of the filled syringes, which is at least as great as the pressure of the syringe contents during autoclaving. The steam/air autoclave has programmable controls which adjust the pressure by air injection during the autoclave cycle in order to maintain the pressure on the outer surfaces at a level at least as great as the pressure of the syringe contents. A suitable programmable steam/air autoclave is commercially available from American Sterilizer Co., Erie, Pa.

Since many variations, modifications and changes in detail may be made to the above-described embodiments without departing from the scope and spirit of the invention, it is intended that all matter described above and shown in the accompanying drawings be interpreted as only illustrative of one or more of many possible embodiments of the invention which is defined in the following claims.

What is claimed is:

1. A method of producing a prefilled, sterile plastic syringe having a molded plastic barrel with an open end and a nozzle at the opposite end, a tip seal closing the nozzle, and a piston slidable in the barrel and sealing the open end of the barrel to retain a liquid therein; the method comprising the steps of:

removing debris and other contaminants from the tip seal and piston;

destroying microbial contaminants on the tip seal and piston;

washing the barrel with a sequence of a multiplicity of jets of water to remove debris and pyrogens from the barrel;

applying a lubricant to the tip seal, piston and barrel;

assembling the tip seal on the nozzle of the barrel;

filling the barrel through its open end with a desired quantity of liquid material;

assembling the piston in the open end of the barrel after the filling thereof to complete the enclosure and sealing of the syringe and its contents; and autoclaving the assembled and sealed syringe to sterilize the plastic syringe and its contents, while maintaining a pressure on the outside surfaces of the syringe at least equal to the pressure of the syringe contents during autoclaving.

2. A method as claimed in claim 1 wherein the filling of the barrel includes filing the barrel with a liquid contrast media.

3. A method as claimed in claim 1 wherein the autoclaving of the assembled and sealed syringe is performed by heating the assembled and sealed syringe to a temperature in the range of 120° to 125° C. to reach an $F_o$ of approximately 20.

* * * * *